(12) United States Patent
Hamprecht et al.

(10) Patent No.: US 6,407,245 B2
(45) Date of Patent: Jun. 18, 2002

(54) SUBSTITUTED THIOPYRIDINES

(75) Inventors: Gerhard Hamprecht, Weinheim; Joachim Gebhardt, Wachenheim; Heinz Isak, Böhl-Iggelheim; Michael Rack, Heidelberg; Joachim Rheinheimer, Ludwigshafen; Peter Schäfer, Ottersheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/791,688

(22) Filed: Feb. 26, 2001

Related U.S. Application Data

(62) Division of application No. 09/254,569, filed as application No. PCT/EP97/04707 on Aug. 29, 1997.

(30) Foreign Application Priority Data

Sep. 12, 1996 (DE) .......................... 196 36 997

(51) Int. Cl.$^7$ ................... C07D 213/71; C07D 213/70
(52) U.S. Cl. ........................... 546/295; 546/303
(58) Field of Search ................. 546/295, 303

(56) References Cited

U.S. PATENT DOCUMENTS

| | | | |
|---|---|---|---|
| 4,946,854 A | 8/1990 | Maienfisch et al. | 514/346 |
| 4,983,211 A | 1/1991 | Markley et al. | 71/94 |
| 5,468,863 A | 11/1995 | Pfirmann et al. | 546/345 |
| 6,191,280 B1 * | 2/2001 | Hamprecht et al. | 546/294 |

FOREIGN PATENT DOCUMENTS

| | | |
|---|---|---|
| DE | 19636995 | 3/1998 |
| EP | 498396 | 8/1992 |
| JP | 56029504 | 3/1981 |
| JP | 60185764 | 9/1985 |
| JP | 60188370 | 9/1985 |
| WO | 92/15576 | 9/1992 |
| WO | 95/02580 | 1/1995 |
| WO | 98/54137 | 12/1998 |
| WO | 98/54139 | 12/1998 |

OTHER PUBLICATIONS

Bordwell et al. "The Formation of α–Chloro–Sufides from Sulfides and from Sulfoxides" JACS No. 77, (1955) pp 572–577.
Petric et al. "Oxidative Transformations of Some Azinyl Sulfides" Chimia No. 29 (1975) p 466.
J. Sci. Ind. Res., 2lb, pp. 483–486, 1962.
Phosphorus and Sulfur, 34, pp. 123–132, 1987.
Heterocycles, 24(12), pp. 3337–3340, 1986.
Angew. Chem. Ind. Ed. Engl. 33(13), pp. 1386–1389, 1994.
Tetra. Letters, 32(25), pp. 2943–2946, 1991.
Heterocycles, 22(1), pp. 117–124, 1984.
Houben–Weyl, Meth. der Organ. Chem., vol. IV/1a, 4th Ed., 1981, pp. 304–308.
Houben–Weyl, Meth. der Organ. Chem., vol. E7b, 4th Ed., 1992, pp. 565–566.
Tetra. Letters, 32(28), pp. 3309–3312 (1991).
Chem. Pharm. Bull, 38(12) pp. 3359–3365, 1990.
Org. Prep. Proced. Int., 26(3), pp. 349–352 (1994).
J. Prakt. Chem., 332(5), pp. 679–686, 1990.
Pharmazie, 45(9), pp. 657–659, 1990.
Synthetic Commun., 21(2), pp. 211–214, 1991.
Coll. Czech. Chem. Commun., 50, pp. 2179–2190, 1985.
Petrol. Chem., 34(4), pp.347–352, 1994.
J. Org. Chem., 28, p.2485–86, 1963.
J. Am. Chem. Soc., 77, p.72–577, 1955.
J. Am. Chem. Soc., 78, p 5008–5011, 1956.
Tetra. Letters, 23, p. 2363–2366, 1972.

* cited by examiner

Primary Examiner—Charanjit S. Aulakh
(74) Attorney, Agent, or Firm—Keil & Weinkauf

(57) ABSTRACT

Substituted thiopyridines of the general formula I

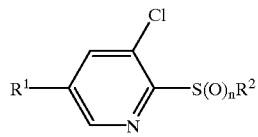

where
  n is 1 or 2;
  $R^1$ is chlorine, $C_1$–$C_3$-fluoroalkyl, nitro or methylsulfonyl;
  $R^2$ is a $C_1$–$C_{10}$-alkyl, $C_2$–$C_{10}$-alkenyl or $C_2$–$C_{10}$-alkynyl radical, in each case unsubstituted or substituted by halogen, $C_1$–$C_4$-alkoxy, $C_1$–$C_4$-alkoxycarbonyl, di-($C_1$–$C_4$-alkylamino)carbonyl, cyano or nitro, a $C_3$–$C_8$-cycloalkyl radical, or a $C_1$–$C_4$-alkyl-enephenyl, phenyl or naphthyl radical which is unsubstituted or substituted in the phenyl moiety by halogen, $C_1$–$C_3$-alkyl, $C_1$–$C_3$-alkoxy, trifluoromethyl, cyano or nitro.

5 Claims, No Drawings

SUBSTITUTED THIOPYRIDINES

The present application is a divisional of application Ser. No. 09/254,569, filed as PCT/EP 97/04707 on Aug. 29, 1997.

The invention relates to novel thiopyridines of the general formula I

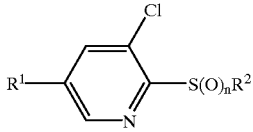

where
n is 1 or 2;
$R^1$ is chlorine, $C_1-C_3$-fluoroalkyl, nitro or methylsulfonyl;
$R^2$ is a $C_1-C_{10}$-alkyl, $C_2-C_{10}$-alkenyl or $C_2-C_{10}$-alkynyl radical, in each case unsubstituted or substituted by halogen, $C_1-C_4$-alkoxy, $C_1-C_4$-alkoxycarbonyl, di-($C_1-C_4$-alkylamino)carbonyl, cyano or nitro, a $C_3-C_8$-cycloalkyl radical, or a $C_1-C_4$-alkylenephenyl, phenyl or naphthyl radical which is unsubstituted or substituted in the phenyl moiety by halogen, $C_1-C_3$-alkyl, $C_1-C_3$-alkoxy, trifluoromethyl, cyano or nitro.

Moreover, the invention relates to processes for their preparation and to their use as intermediates for the preparation of herbicidally active crop protection agents, as they are disclosed in WO-A-95/02580. The invention furthermore relates to the pyridine thioethers of the formula Ia, which are suitable for the preparation of the thiopyridines I, as intermediates.

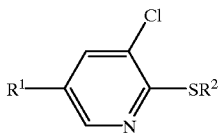

2-(3-Nitrophenylthio), 2-(2-methyl-4-methoxyphenylthio) and 2-(2-nitrobenzylthio)pyridines which have a further chlorine, or trifluoromethyl or methylsulfonyl radical, in the 5-position and a chlorine substituent in the 3-position have already been disclosed in the literature (EP 320 448, J5 6029-504, EP 498 396) 3-Fluoropyridines which are correspondingly substituted are disclosed in U.S. Pat. No. 4,983, 211.

The thiopyridines mentioned in the above publications are used as herbicides or fungicides, or as intermediates for herbicides, the function which is responsible for the herbicidal action in the end molecule being synthesized in each case via the thio substituent, which thus remains in the end molecule.

It is an object of the present invention to provide novel thiopyridine derivatives which are suitable as coupling components for the preparation of substituted phenylpyridines as they are described in WO-A-95/02580. Here, the thio substituent acts as a leaving group.

It is a further object of the present invention to provide a process which makes the desired thiopyridines accessible in high yields.

Accordingly, we have found the thiopyridines defined at the out-set, of the general formula I

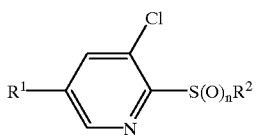

where
n is 1 or 2;
$R^1$ is chlorine, $C_1-C_3$-fluoroalkyl, nitro or methylsulfonyl;
$R^2$ is a $C_1-C_{10}$-alkyl, $C_2-C_{10}$-alkenyl or $C_2-C_{10}$-alkynyl radical, in each case unsubstituted or substituted by halogen, $C_1-C_4$-alkoxy, $C_1-C_4$-alkoxycarbonyl, di-($C_1-C_4$-alkylamino)carbonyl, cyano or nitro, a $C_3-C_8$-cycloalkyl radical, or a $C_1-C_4$-alkylenephenyl, phenyl or naphthyl radical which is unsubstituted or substituted in the phenyl moiety by halogen, $C_1-C_3$-alkyl, $C_1-C_3$-alkoxy, trifluoromethyl, cyano or nitro.

The meanings mentioned above for the substituent $R^2$ in formula I are collective terms for individual enumerations of the individual group members. All carbon chains, ie. all alkyl, alkenyl, alkynyl or alkoxy moieties, can be straight-chain or branched.

Halogenated substituents preferably have attached to them 1–6 identical or different halogen atoms.

Examples of individual meanings are:
halogen fluorine, chlorine, bromine and iodine, preferably fluorine and chlorine;
$C_1-C_3$-alkyl methyl, ethyl, n-propyl, 1-methylethyl;
$C_1-C_{10}$-alkyl $C_1-C_3$-alkyl as mentioned above, and also n-butyl, 1-methylpropyl, 2-methylpropyl and 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-2-methylpropyl; n-heptyl, n-octyl, n-nonyl, n-decyl, 1-methylhexyl, 1-ethylhexyl, 1-methylheptyl, 1-methyloctyl, 1-methylnonyl;
$C_2-C_{10}$-alkenyl ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, hept-2-en-1-yl, oct-2-en-1-yl, non-2-en-1-yl, dec-2-en-1-yl, preferably ethenyl and prop-2-en-1-yl;

$C_2$–$C_{10}$-alkynyl ethynyl and $C_3$–$C_6$-alkynyl such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, hept-2-yn-1-yl, oct-2-yn-1-yl, non-2-yn-1-yl, dec-2-yn-1-yl, preferably prop-2-yn-1-yl, 1-methylprop-2-yn-1-yl;

$C_1$–$C_3$-fluoroalkyl $C_1$–$C_3$-alkyl as mentioned above, where in each case 1–5 hydrogen atoms are replaced by fluorine, eg. fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluoropropyl, preference is given to difluoromethyl, trifluoromethyl, 2,2,2-trifluoroethyl, pentafluoroethyl, 3,3,3-trifluoropropyl, special preference is given to trifluoromethyl;

$C_1$–$C_{10}$-haloalkyl $C_1$–$C_{10}$-alkyl as mentioned above, where in each case 1–6 hydrogen atoms are replaced by fluorine, chlorine and/or bromine, ie., for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

$C_2$–$C_{10}$-haloalkenyl $C_2$–$C_{10}$-alkenyl as mentioned above, where in each case 1–6 hydrogen atoms are replaced by fluorine, chlorine and/or bromine;

$C_2$–$C_{10}$-haloalkynyl $C_2$–$C_{10}$-alkynyl as mentioned above, where in each case one to six hydrogen atoms are replaced by fluorine, chlorine and/or bromine;

$C_3$–$C_8$-cycloalkyl cyclopropyl, cyclobutyl, cyclopentyl, cyclohexyl, cycloheptyl and cyclooctyl, preferably cyclopropyl, cyclopentyl and cyclohexyl;

cyano-($C_1$–$C_{10}$)-alkyl $C_1$–$C_{10}$-alkyl as mentioned above, where in each case one hydrogen atom is replaced by the cyano group, ie., for example, cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methyl-prop-3-yl, 2-cyano-2-methyl-prop-3-yl, 3-cyano-2-methyl-prop-3-yl, and 2-cyanomethyl-prop-2-yl, 6-cyanohex-1-yl, 7-cyanohept-1-yl, 8-cyanooct-1-yl, 9-cyanonon-1-yl, 10-cyanodec-1-yl; preferably cyanomethyl, 1-cyano-1-methylethyl;

$C_1$–$C_4$-alkoxy and the alkoxy moieties of $C_1$–$C_4$-alkoxycarbonyl, methoxy, ethoxy, n-propoxy, 1-methylethoxy, n-butoxy, 1-methylpropoxy, 2-methylpropoxy and 1,1-dimethyl-ethoxy, preferably methoxy, ethoxy and 1-methylethoxy;

di-($C_1$–$C_4$-alkyl) aminocarbonyl N,N-dimethylaminocarbonyl, N,N-diethylaminocarbonyl, N,N-dipropylaminocarbonyl, N,N-di-(1-methylethyl) aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl) aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl) aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1dimethylethyl)aminocarbonyl, N-(1-methylethyl)-N-propylaminocarbonyl, N-butyl-N-propylaminocarbonyl, N-(1-methylpropyl)-N-propylarinocarbonyl, N-(2-methylpropyl)-N-propylaminocarbonyl, N-(1-dimethylethyl)-N-propylaminocarbonyl, N-butyl-N-(1-methylethyl) aminocarbonyl, N-(1-methylethyl)-N-(1-methylpropyl) aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl) aminocarbonyl, preferably dimethylaminocarbonyl and diethylaminocarbonyl;

$C_1$–$C_4$-alkylene methylene, ethylene, propylene, 1-methylethylene, butylene, 1,2-dimethylethylene and 1-ethylethylene;

1-phenyl which is unsubstituted or substituted by halogen, $C_1$–$C_3$-alkyl, $C_1$–$C_3$-alkoxy, trifluoromethyl, cyano or nitro 2-, 3-, 4-chlorophenyl, 2-, 3-, 4-tolyl, 2-chloro-4-methylphenyl, 2,4-dichlorophenyl, 2,4,6-trichlorophenyl, 2,6-dichloro-4-methylphenyl, 2-, 3-, 4-methoxyphenyl, 2-chloro-4-methoxyphenyl, 20 3-chloro-4-methoxyphenyl, 2-, 3-, 4-trifluoromethylphenyl, 2-, 3-, 4-cyanophenyl, 2-, 3-, 4-nitrophenyl, 2-methyl-4-nitrophenyl, 2-chloro-4-trifluoromethylphenyl, 2-chloro-4-nitrophenyl and unsubstituted phenyl.

Preferred amongst the compounds I are those where n is 1 or 2;

$R^1$ is chlorine, nitro or $C_1$–$C_3$-fluoroalkyl;

$R^2$ is a $C_1$–$C_8$-alkyl, $C_2$–$C_8$-alkenyl or $C_3$–$C_8$-alkynyl radical, unsubstituted or substituted by halogen or $C_1$–$C_4$-alkoxy, an unsubstituted $C_3$–$C_8$-cycloalkyl radical, or a benzyl or phenyl radical, unsubstituted or substituted in the phenyl moiety by halogen, $C_1$–$C_3$-alkyl, $C_1$–$C_3$-alkoxy, nitro, cyano or trifluoromethyl.

Especially preferred compounds I are those where n is 1 or 2;

$R^1$ is chlorine, trifluoromethyl or difluoromethyl; $R^2$ is a $C_1$–$C_8$-alkyl radical, unsubstituted or substituted by chlorine or methoxy, or a benzyl or phenyl radical, unsubstituted or substituted in the phenyl moiety by chlorine, methyl, methoxy or trifluoromethyl.

Individual examples which may be mentioned are the following pyridine thioethers Ia of Tables 1–4, the pyridine sulfoxides Ib of Tables 5–8 and the pyridine sulfones Ic of Tables 9–12.

Preferred are the pyridine thioethers 1.001–1.116 of the formula Ia1

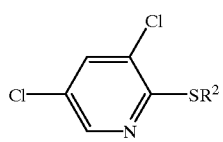

Ia1 which are given in Table 1.

TABLE 1

| No. | $R^2$ |
|---|---|
| Ia1.001 | $CH_3$ |
| Ia1.002 | $C_2H_5$ |
| Ia1.003 | n-$C_3H_7$ |
| Ia1.004 | i-$C_3H_7$ |
| Ia1.005 | n-$C_4H_9$ |
| Ia1.006 | sec-$C_4H_9$ |
| Ia1.007 | i-$C_4H_9$ |
| Ia1.008 | tert-$C_4H_9$ |
| Ia1.009 | n-$C_5H_{11}$ |
| Ia1.010 | sec-$C_5H_{11}$ |
| Ia1.011 | $CH_2$—$CH_2$—$CH(CH_3)_2$ |
| Ia1.012 | $CH_2$—$CH(CH_3)$—$CH_2$—$CH_3$ |
| Ia1.013 | $CH(CH_3)$—$CH(CH_3)_2$ |
| Ia1.014 | $CH(C_2H_5)_2$ |
| Ia1.015 | n-$C_6H_{13}$ |
| Ia1.016 | sec-$C_6H_{13}$ |
| Ia1.017 | $CH(C_2H_5)$-n-$C_3H_7$ |
| Ia1.018 | $CH(CH_3)$—$CH(CH_3)$—$C_2H_5$ |
| Ia1.019 | n-$C_7H_{15}$ |
| Ia1.020 | sec-$C_7$—$H_{15}$ |
| Ia1.021 | $CH(C_2H_5)$-n-$C_4H_9$ |
| Ia1.022 | $CH(CH_3)$—$CH(CH_3)$-n-$C_3H_7$ |
| Ia1.023 | n-$C_8H_{17}$ |
| Ia1.024 | sec-$C_8H_{17}$ |
| Ia1.025 | $CH(C_2H_5)$-n-$C_5H_{11}$ |
| Ia1.026 | n-$C_9H_{19}$ |
| Ia1.027 | sec-$C_9H_{19}$ |
| Ia1.028 | $CH(C_2H_5)$-n-$C_6H_{13}$ |
| Ia1.029 | n-$C_{10}H_{21}$ |
| Ia1.030 | sec-$C_{10}H_{21}$ |
| Ia1.031 | $CH_2$—$CH_2$—O—$CH_3$ |
| Ia1.032 | $CH_2$—$CH_2$—O—$C_2H_5$ |
| Ia1.033 | $CH_2$—$CH(OCH_3)$—$CH_3$ |
| Ia1.034 | $(CH_2)_3$—O—$CH_3$ |
| Ia1.035 | $(CH_2)_3$—O—$C_2H_5$ |
| Ia1.036 | $(CH_2)_4$—O—$CH_3$ |
| Ia1.037 | $CH_2CH_2Cl$ |
| Ia1.038 | $(CH_2)_3Cl$ |
| Ia1.039 | $(CH_2)_4Cl$ |
| Ia1.040 | cyclopropyl |
| Ia1.041 | cyclobutyl |
| Ia1.042 | cyclopentyl |
| Ia1.043 | cyclohexyl |

TABLE 1-continued

| No. | $R^2$ |
|---|---|
| Ia1.044 | cycloheptyl |
| Ia1.045 | cyclooctyl |
| Ia1.046 | $CH_2$=$CH_2$ |
| Ia1.047 | $CH_2$—$CH$=$CH_2$ |
| Ia1.048 | $CH_2CH$=$CH$—$CH_3$ |
| Ia1.049 | $CH(CH_3)$—$CH$=$CH_2$ |
| Ia1.050 | $CH_2$—$CH_2$—$C(CH_3)$=$CH_2$ |
| Ia1.051 | $CH_2CH$=$C(CH_3)_2$ |
| Ia1.052 | $C(CH_3)_2$—$CH$=$CH_2$ |
| Ia1.053 | $CH_2$—$C$≡$CH$ |
| Ia1.054 | $CH_2$—$C$≡$C$—$CH_3$ |
| Ia1.055 | $CH(CH_3)$—$C$≡$CH$ |
| Ia1.056 | $C(CH_3)_2$—$C$≡$H$ |
| Ia1.057 | $C(C$≡$CH)$—$CH(C_2H_5)$-n-$C_4H_9$ |
| Ia1.058 | $CH_2$—$CH_2$—$CN$ |
| Ia1.059 | $(CH_2)_3CN$ |
| Ia1.060 | $CH_2CH_2NO_2$ |
| Ia1.061 | $(CH_2)_3NO_2$ |
| Ia1.062 | phenyl |
| Ia1.063 | 2-chlorophenyl |
| Ia1.064 | 3-chlorophenyl |
| Ia1.065 | 4-chlorophenyl |
| Ia1.066 | 2,3-dichlorophenyl |
| Ia1.067 | 2,4-dichlorophenyl |
| Ia1.068 | 2,5-dichlorophenyl |
| Ia1.069 | 2,6-dichlorophenyl |
| Ia1.070 | 2,4,6-trichlorophenyl |
| Ia1.071 | 2-tolyl |
| Ia1.072 | 3-tolyl |
| Ia1.073 | 4-tolyl |
| Ia1.074 | 2-chloro-4-tolyl |
| Ia1.075 | 2,6-dichloro-4-tolyl |
| Ia1.076 | 4-chloro-2-tolyl |
| Ia1.077 | 4,6-dichloro-2-tolyl |
| Ia1.078 | 2-methoxyphenyl |
| Ia1.079 | 3-methoxyphenyl |
| Ia1.080 | 4-methoxyphenyl |
| Ia1.081 | 2-chloro-4-methoxyphenyl |
| Ia1.082 | 2,6-dichloro-4-methoxyphenyl |
| Ia1.083 | 4-chloro-2-methoxyphenyl |
| Ia1.084 | 4 6-dichloro-2-methoxyphenyl |
| Ia1.085 | 2-nitrophenyl |
| Ia1.086 | 3-nitrophenyl |
| Ia1.087 | 4-nitrophenyl |
| Ia1.088 | 4-methyl-2-nitrophenyl |
| Ia1.089 | 4-chloro-2-nitrophenyl |
| Ia1.090 | 4-methoxy-2-nitrophenyl |
| Ia1.091 | 2-trifluoromethylphenyl |
| Ia1.092 | 3-trifluoromethylphenyl |
| Ia1.093 | 4-trifluoromethylphenyl |
| Ia1.094 | 2-chloro-4-trifluoromethylphenyl |
| Ia1.095 | 4-chloro-2-trifluoromethylphenyl |
| Ia1.096 | 2-cyanophenyl |
| Ia1.097 | 3-cyanophenyl |
| Ia1.098 | 4-cyanophenyl |
| Ia1.099 | 2-methyl-4-nitrophenyl |
| Ia1.100 | 5-methyl-2-nitrophenyl |
| Ia1.101 | 1-naphthyl |
| Ia1.102 | 2-naphthyl |
| Ia1.103 | 4-methyl-1-naphthyl |
| Ia1.104 | 4-chloro-1-naphthyl |
| Ia1.105 | benzyl |
| Ia1.106 | 2-methylbenzyl |
| Ia1.107 | 3-methylbenzyl |
| Ia1.108 | 4-methylbenzyl |
| Ia1.109 | 2-chlorobenzyl |
| Ia1.110 | 3-chlorobenzyl |
| Ia1.111 | 4-chlorobenzyl |
| Ia1.112 | 2,4-dichlorobenzyl |
| Ia1.113 | 2,4,6-trichlorobenzyl |
| Ia1.114 | 2-trifluoromethylbenzyl |
| Ia1.115 | 3-trifluoromethylbenzyl |
| Ia1.116 | 4-trifluoromethylbenzyl |

Table 2

Furthermore preferred are the pyridine thioethers Ia2.001–Ia2.085 and Ia2.087–Ia2.116 of the formula Ia2, which differ from the compounds Ia1.001–Ia1.085 and Ia1.087–Ia1.116 in that, instead of chlorine, a trifluoromethyl group is attached to the pyridine ring in the 5-position.

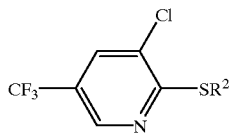

Ia2

Table 3
Furthermore preferred are the pyridine thioethers Ia3.001–Ia3.116 of the formula Ia3, which differ from the compounds Ia1.001–Ia1.116 in that a methylsulfonyl group is attached to the pyridine ring in the 5-position.

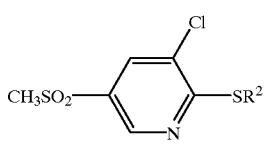

Ia3

Table 4
Furthermore preferred are the pyridine thioethers Ia4.001–Ia4.116 of the formula Ia4, which differ from the compounds Ia1.001–Ia1.116 in that a difluoromethyl group is attached to the pyridine ring in the 5-position.

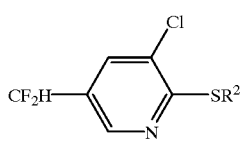

Ia4

Table 5
Furthermore preferred are the thiopyridines Ib1.001–Ib1.116 of the formula Ib1, which differ from the compounds Ia1.001–Ia1.116 in that the corresponding sulfoxides are present.

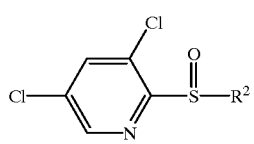

Ib1

Table 6
Furthermore preferred are the thiopyridines Ib2.001–Ib2.116 of the formula Ib2, which differ from the compounds Ia2.001–Ia2.116 in that the corresponding sulfoxides are present.

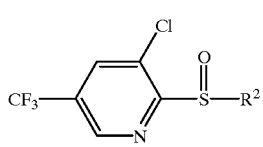

Ib2

Table 7
Furthermore preferred are the thiopyridines Ib3.001–Ib3.116 of the formula Ib3, which differ from the compounds Ia3.0001–Ia3.116 in that the corresponding sulfoxides are present.

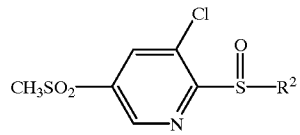

Ib3

Table 8
Furthermore preferred are the thiopyridines Ib4.001–Ib4.116 of the formula Ib4, which differ from the compounds Ia4.001–Ia4.116 in that the corresponding sulfones are present.

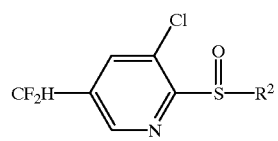

Ib4

Table 9
Furthermore preferred are the thiopyridines Ic1.001–Ic1.116 of the formula Ic1, which differ from the compounds Ia1.001–Ia1.116 in that the corresponding sulfones are present.

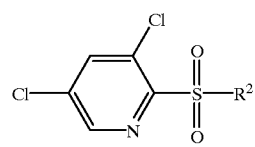

Ic1

Table 10
Furthermore preferred are the thiopyridines Ic2.001–Ic2.116 of the formula Ic2, which differ from the compounds Ia2.001–Ia2.116 in that the corresponding sulfones are present.

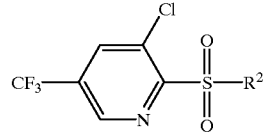

Ic2

Table 11
Furthermore preferred are the thiopyridines Ic3.001–Ic3.116 of the formula Ic3, which differ from the compounds Ia3.001–Ia3.116 in that the corresponding sulfones are present.

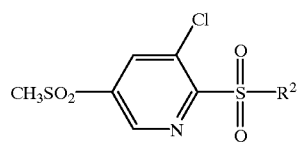

Ic3

Table 12
Furthermore preferred are the thiopyridines Ic4.001–Ic4.116 of the formula Ic4, which differ from the compounds Ia4.001–Ia4.116 in that the corresponding sulfones are present.

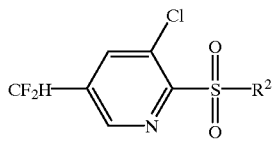

Ic4

Furthermore, processes have been found with which the thiopyridines of the formula I can be prepared in surprisingly high yields.

The thiopyridines I are especially preferably obtained when substituted 3-chloro-2-halopyridines of the formula II

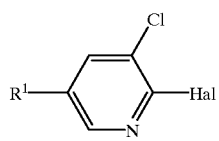

II where $R^1$ has the abovementioned meaning and Hal is fluorine, chlorine or bromine are reacted, in a first step, with a thio compound of the formula III

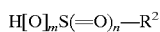 III where $R^2$ has the abovementioned meaning and m and n are 0, or with an alkali metal or alkaline earth metal salt thereof, in the presence or absence of a base, first to give a pyridine thioether of the formula Ia and the latter is then oxidized stepwise to the sulfoxide Ib

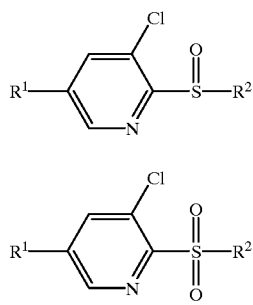

Ib

Ic or sulfone Ic, or when the 3-chloro-2-halopyridines of the formula II are directly reacted with a sulfinic acid of the formula III, where $R^2$ has the abovementioned meaning and m and n are 1, or with an alkali metal or alkaline earth metal salt thereof, in the presence or absence of a base, to give the pyridylsulfones of the formula Ic. A substance which is especially preferably employed as compound II is 2,3-dichloro-5-trifluoromethylpyridine, which is commercially available.

The synthesis of the compounds I is demonstrated by way of example by the reaction described in the scheme below, which starts with 2,3-dichloro-5-trifluoromethylpyridine and propylmercaptan sodium salt as nucleophile, using hydrogen peroxide as the oxidant:

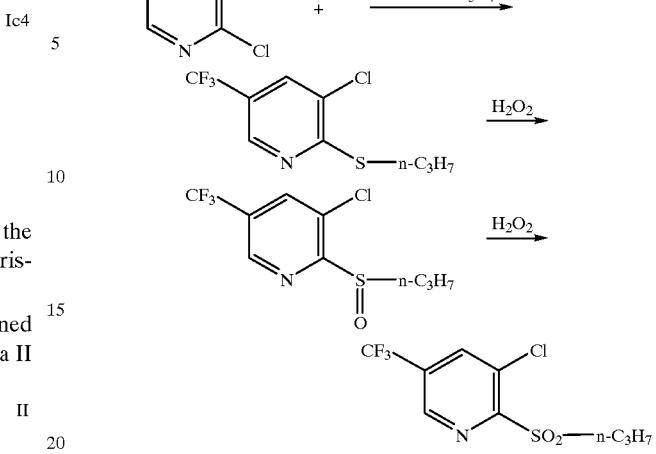

Instead of hydrogen peroxide, peracetic acid or chlorine and bromine may also be used as the oxidant in a method similar to the above equation.

In accordance with a further variant, the compounds I can be prepared starting from 2,3-dichloro-5-trifluoromethylpyridine and a benzenesulfinic acid salt as the nucleophile, as described in the scheme below:

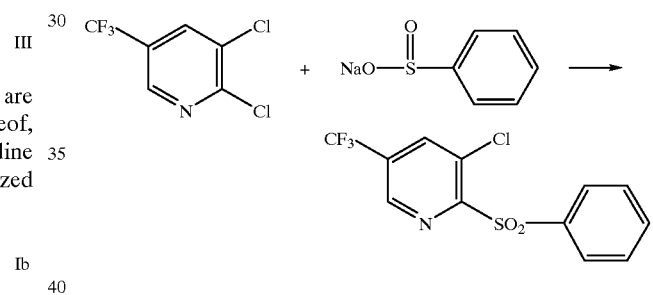

Preferred embodiments of the process are given hereinbelow:

The reaction of the 3-chloro-2-halopyridines II with a thiol III (m,n=0) or with a sulfinic acid III (m,n=1) is advantageously carried out in the presence of a solvent from −20 to 200° C., preferably 10–180° C., particularly preferably from 10 to 80° C. for the thiol and from 80 to 180° C. for the sulfinic acid.

Solvents which are used for these reactions are—depending on the temperature range—hydrocarbons such as pentane, hexane, cyclohexane, heptane, toluene, xylene, chlorinated hydrocarbons such as methylene chloride, 1,2-dichloroethane, 1,1,2,2-tetrachloroethane, chlorobenzene, 1,2-, 1,3- or 1,4-dichlorobenzene, ethers such as diethyl ether, methyl tert-butyl ether, tetrahydrofuran, 1,3- or 1,4-dioxane, anisole, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as DMF, N-methylpyrrolidone, nitrohydrocarbons such as nitromethane, nitroethane, nitropropane and nitrobenzene, ureas such as tetraethylurea, tetrabutylurea, dimethylethyleneurea, dimethylpropyleneurea, sulfoxides such as dimethyl sulfoxide, sulfones such as dimethyl sulfone, diethyl sulfone, tetramethylene sulfone, nitriles such as acetonitrile, propionitrile, butyronitrile or isobutyronitrile; water, or else mixtures of these up to a two-phase system. The process may also be carried out according to the invention in the melt, without the addition of a solvent.

The molar ratios at which the starting compounds are reacted with each other are generally 0.9–1.4, preferably 0.95–1.1, for the ratio of thiol, or sulfinic acid, to 3-chloro-2-halopyridine II. The concentration of the starting materials in the solvent is 0.1–5 mol/l, preferably 0.2–2 mol/l.

The thiols, or sulfinic acids, are expediently employed in the form of their alkali metal or alkaline earth metal salts, ie. their lithium, sodium, potassium, magnesium or calcium salts. However, the reaction can also be carried out in the presence of an organic base, eg. triethylamine, tri-n-propylamine, N-ethyldiisopropylamine, pyridine, α-, β-, γ-picoline, 2,4-, 2,6-lutidine, N-methylpyrrolidine, triethylenediamine, dimethylaniline, N,N-dimethylcyclohexylamine, quinoline or acridine. In addition, it is also possible to bind the hydrogen halide which is eliminated during the reaction by adding an alkali metal hydride, alkali metal hydrogencarbonate, alkali metal carbonate, alkaline earth metal hydride, alkaline earth metal hydrogencarbonate or alkaline earth metal carbonate of the abovementioned metals. The thiols, or sulfinic acids, are advantageously converted into their corresponding salts using one of the abovementioned bases in an inert solvent, to be followed by the reaction with the 3-chloro-2-halopyridine. Depending on the reactivity of the sulfur derivatives used, the water formed during salt formation may be left in the reaction medium, or else removed azeotropically with a solvent. Salt formation may also be carried out in an aqueous phase to start with, whereupon the water is removed. The salt formation may also be carried out with an alkali metal hydride, alkali metal alkoxide, alkaline earth metal hydride or alkaline earth metal alkoxide, preferably sodium methoxide or sodium ethoxide, and the excess alcohol removed prior to the reaction with the pyridine.

Finally, the reaction can also be carried out in an aqueous two-phase system, preferably in the presence of phase-transfer catalysts, such as quaternary ammonium or phosphonium salts. The reaction conditions described in EP-A-556 737 are suitable for the two-phase reaction.

It is advantageous to add the 3-chloro-2-halopyridine II to a mixture of the thiol III or the sulfinic acid III or the respective salt in one of the abovementioned solvents at from 10 to 80° C. in the course of 0.25–2 hours and to stir for a further 20 0.5 to 16 hours, preferably 2 to 8 hours, at from 10 to 80° C. in the case of the thiol respectively at from 80 to 180° C. in the case of the sulfinic acid so as to complete the reaction.

However, it is also possible to add the thiol III or the sulfinic acid III together or, via separate feeding, in parallel with the addition of the base to the 3-chloro-2-halopyridine II and then to finish the reaction as above.

When using an aqueous two-phase system, the starting materials II and III can be added to a mixture of the phase-transfer catalyst in the two phases in any sequence, with stirring, and then the reaction can be finished in the abovementioned temperature range with an addition of base.

The reaction can be carried out under atmospheric pressure or superatmospheric pressure, continuously or batchwise.

The pyridine thioethers of the formula Ia can be oxidized to the thiopyridines I preferably by means of hydrogen superoxide, approximately equivalent amounts of oxidant giving the pyridine sulfoxides Ib and approximately twice the molar amounts giving the pyridine sulfones Ic.

Solvents which can be used are, for example, water, acetonitrile, carboxylic acids such as acetic acid, trifluoroacetic acid, propionic acid, alcohols such as methanol, ethanol, isopropanol, tert-butanol, chlorinated hydrocarbons such as methylene chloride, 1,1,2,2-tetrachloroethane or ketones such as acetone or methyl ethyl ketone. Especially preferred are water, methanol, acetic acid and trifluoroacetic acid.

In an especially preferred variant, the reaction can also be catalyzed by adding stronger acids such as trifluoroacetic acid or perchloric acid. However, metal compounds are also suitable as catalysts, eg. transition metal oxides such as vanadium pentaoxide, sodium tungstate, potassium dichromate, iron oxide tungstate, sodium tungstate molybdic acid, osmic acid, titanium trichloride, selenium dioxide, phenyleneselenic acid, oxovanadinyl 2,4-pentanedionate.

The catalysts are generally employed in an amount of from 0.5 to 10%, but it is also possible to employ stoichiometric amounts due to the fact that the inorganic catalysts are readily filtered off and recovered.

A further preferred oxidant is peracetic acid or hydrogen superoxide/acetic anhydride, if appropriate also the peracetic acid which exists in equilibrium with a hydrogen superoxide/acetic acid mixture.

Another preferred oxidant is trifluoroperacetic acid, or the mixture hydrogen superoxide/trifluoroacetic acid, or else the mixture hydrogen peroxide/trifluoroacetic anhydride.

In general, oxidation with hydrogen superoxide in glacial acetic acid is highly selective, but frequently slow. In general, the reaction time can be shortened by adding trifluoroacetic acid (cf. Synthesis Example 5, Variant a and b). The oxidation with hydrogen peroxide in pure trifluoroacetic acid frequently leads to the formation of the corresponding N-oxides, as described, inter alia, in Chimia 29 (1975) 466. Rapid and selective oxidation of the pyridine thioethers Ia to the corresponding sulfoxides Ib and sulfones Ic is successfully carried out for example with solutions of hydrogen superoxide in mixtures of acetic acid and trifluoroacetic acid in a volumetric ratio of 10:1 to 1:1, in particular 6:1 to 4:1. These mixtures are therefore especially preferred as solvents.

Solvents which can furthermore be used are petroleum ether, the abovementioned solvents, and the abovementioned catalysts.

In addition to peracetic acid and trifluoroperacetic acid, it is also possible to employ perbenzoic acid, monoperphthalic acid or 3-chloroperbenzoic acid, expediently in chlorinated hydrocarbons such as methylene chloride or 1,2-dichloroethane.

Highly suitable for the oxidation of the thiols to sulfoxides or sulfones are furthermore chlorine and bromine. Advantageous solvents are water, acetonitrile, dioxane, two-phase systems such as aqueous potassium hydrogen carbonate solution/dichloromethane and, in the case of pyridine alkyl thioethers, also acetic acid.

Other substances which can be employed as sources of active halogen are tert-butyl hypochlorite, hypochlorous and hypobromous acid, their salts, and furthermore N-halogen compounds such as N-bromo- and N-chlorosuccinimide, or else sulfuryl chloride.

Other substances which are advantageous for the oxidation are dinitrogen tetraoxide, eg. in the technologically simple variant with air/nitrogen dioxide or nitrogen trioxide and, for example, osmium(VIII) oxide as catalyst. In addition, the oxidation can also be carried out directly with nitric acid, suitable additional solvents being acetic anhydride, acetic acid, and suitable catalysts being copper(I) bromide, copper(I) chloride, copper(II) bromide and copper (II) chloride.

Also suitable for the oxidation is photo-sensitized oxygen transfer, recommended photosensitizers being chlorophyll, protoporphyrin, rose bengal or methylene blue. Suitable inert solvents are hydrocarbons such as pentane, hexane, heptane, cyclohexane, chlorinated hydrocarbons such as methylene chloride, 1,2-dichloroethane, 1,1,2,2-tetrachloroethane, alcohols such as methanol, ethanol, n-propanol or isopropanol, ketones such as acetone, methyl ethyl ketone, polar aprotic solvents such as acetonitrile, propionitrile or aromatic hydrocarbons such as benzene, toluene, chlorobenzene or xylene. Instead of oxygen, it is also possible to use ozone in the abovementioned solvents, and additionally also ethers, 1,4-dioxane or THF.

In addition to photosensitization, it is also recommended to use catalysts for the oxidation, for example oxides and sulfides of nickel, copper, aluminum, tungsten, chromium, vanadium, ruthenium, titanium, manganese, molybdenum, magnesium and iron.

Depending on the stoichiometry of the oxidants used, the result is either the pyridine sulfoxides Ib or their pyridine sulfones Ic. The molar ratios in which the starting compounds are reacted with each other are generally 0.9–1.8, preferably 1.05–1.3 for the ratio of pyridine thioether Ia to oxidant in the case of the oxidation to the pyridine sulfoxide, and generally 1.9–3.5, preferably 2.05–2.9, in the case of the oxidation to the pyridine sulfone.

The concentration of starting materials in the solvent is generally 0.1–5 mol/l, preferably 0.2–2 mol/l.

It is advantageous to introduce the pyridine thioether or the pyridine sulfoxide, if appropriate together with one of the abovementioned catalysts, into one of the abovementioned solvents and then to add the oxidant in the course of 0.25–20 hours, with stirring. The addition and reaction temperature depend on the optimal efficacy of the oxidants in question and the avoidance of secondary reactions. If photosensitized oxygen is used, the process is generally carried out at from −20 to 80° C., but if metal catalysis is used, the process is generally carried out at from 50 to 140° C., and when ozone is used generally at from −78 to 60° C. Due to the limited solubility of the oxygen derivatives, they have to be passed continuously into the reaction mixture over a prolonged period (up to 20 hours) until oxidation on the sulfoxide or sulfone level is complete. If air/nitrogen dioxide or nitrogen trioxide is used, the process is preferably carried out at from 15–150° C. in the course of 1–15 hours. Liquid or readily soluble oxidants such as hydrogen peroxide, peracetic acid, or trifluoroperacetic acid, which is formed together with acetic anhydride or in equilibrium with acetic acid and/or trifluoroperacetic acid, respectively, or hypochlorous acid or hypobromous acid, tert-butyl hypochlorite, chlorine or bromine, N-chloro-, or N-bromosuccinimide or nitric acid can be added to the reaction mixture of the pyridine thioether or pyridine sulfoxide within shorter periods in the course of 0.25–6 hours, depending on the exothermal character of the reaction, to complete the reaction after a further 1–60 hours. Also preferred is a staggered addition of the liquid or dissolved oxidant. In the case of hydrogen superoxide and peracetic acid, or trifluoroperacetic acid, the process is generally carried out at 0–90° C., if tert-butyl hypochlorite is used, generally at from −78 to 30° C., if N-halogen compounds are used, in general at 0–30° C. and if nitric acid is used in general at from 20 to 140° C. In the case of chlorine or bromine, a reaction temperature of 0–40° C. is recommended.

The oxidation reactions can be carried out under atmospheric pressure or under elevated pressure, continuously or batchwise.

The thiopyridines I according to the invention are valuable precursors for the preparation of crop protection agents, in particular herbicides from the class of the phenylpyridines, as they are described in WO-A 95/02580.

Scheme 1

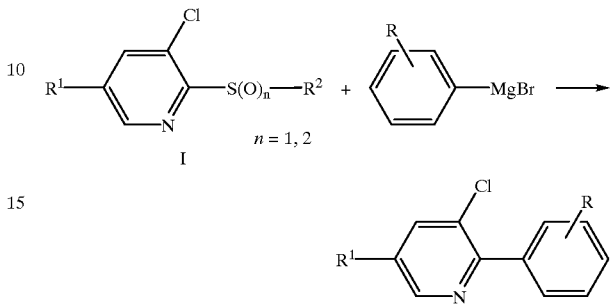

An especially advantageous process for the preparation of herbicidal phenylpyridines based on the thiopyridines I according to the invention is described in a parallel application, DE Application No. 196 36995.9 (see Diagram 1). In addition, the thiopyridines I can also be used as intermediates in organic syntheses for the preparation of pharmaceuticals, colors and the like.

SYNTHESIS EXAMPLES

Example 1

3-Chloro-2-n-propylthio-5-trifluoromethylpyridine 23.8 g (0.313 mol) of 1-propanethiol were added in the course of minutes to a mixture of 7.9 g (0.313 mol) of 95% pure sodium hydride in 200 ml of THF while flushing with nitrogen and stirring, a temperature of 25–30° C. being maintained by means of cooling. After the mixture had been stirred for 1 hour, 54 g (0.25 mol) of 2,3-dichloro-5-trifluoromethylpyridine in 50 ml THF were added at 25–30° C. in the course of 20 minutes with stirring, and stirring was continued for 10 hours at 23° C. The reaction mixture was concentrated in vacuo, taken up in methylene chloride, extracted with 0.5 N sodium hydroxide solution, dried over magnesium sulfate and concentrated, yielding 63.5 g (99.4%) of the title compound of $n^{23}_D$=1.5120.

Example 2

3-Chloro-2-phenylthio-5-trifluoromethylpyridine
Variant a
Starting from 7.9 g (0.313 mol) of sodium hydride, 34.4 g (0.313 mol) of thiophenol and 54 g (0.25 mol) of 2,3-dichloro-5-trifluoromethylpyridine, 72.4 g (100% of theory) of the title compound of $n^{24}_D$=1.5750 were obtained under the conditions of Example 1.
Variant b
108 g (0.981 mol) of thiophenol were added at 20–25° C. with stirring in the course of 1 hour to a mixture of 78.48 g (0.981 mol) of 50% strength sodium hydroxide solution and 800 ml of toluene. After the water had been removed under reflux conditions, 207.45 g (0.9316 mol) of 97% pure 2,3-dichloro-5-trifluoromethylpyridine were added at 80–50° C. in the course of 30 minutes with stirring to the suspension of the above sodium thiophenolate, and stirring was continued for 1 hour at 50° C. and 1 hour at 60° C. The reaction mixture was washed in succession with water, 0.5

N sodium hydroxide solution and with water, dried over sodium sulfate and concentrated in vacuo. This gave 276.2 g of the title compound of $n^{24}_D$=1.5740 which, according to GC analysis, contained a remainder of 2.9% of toluene; Yield 268.2 g (99% of theory).

Example 3

3-Chloro-2-n-propylsulfinyl-5-trifluoromethylpyridine 8.4 g (0.124 mol) of 50% strength hydrogen peroxide were added with stirring at 15–20° C. in the course of 15 minutes to a mixture of 31 g (0.1213 mol) of 3-chloro-2-n-propylthio-5-trifluoromethylpyridine in 150 ml of acetic acid, during which process the temperature rose to 27° C. in the course of 6 hours. After the reaction mixture had been stirred for 14 hours at 25° C., it was poured into ice-water and extracted 3 times with methylene chloride. The organic phase was washed with water and saturated sodium hydrogen carbonate solution, dried and concentrated in vacuo, yielding 32 g (97.2% of theory) of the title compound of m.p. 51–53° C.

Example 4

3-Chloro-2-n-propylsulfonyl-5-trifluoromethylpyridine 11.7 g (0.172 mol) of 50% strength hydrogen peroxide were added at 5 20–25° C. in the course of 30 minutes with stirring to 20 g (0.0783 mol) of 3-chloro-2-n-propylthio-5-trifluoromethylpyridine in 150 ml of glacial acetic acid, during which process the temperature climbed up to 31° C. in the course of 8 hours. After the reaction mixture had been stirred for 60 hours, during which process it cooled to 25° C., it was poured into ice-water and worked up as described. This gave 21 g (93.3% of theory) of the title compound of m.p. 41–42° C.

Example 5

3-Chloro-2-phenylsulfinyl-5-trifluoromethylpyridine
Variant a 6.2 g (0.09 mol) of 50% strength hydrogen superoxide were added at 24° C. in the course of 10 minutes with stirring to a mixture of 22.5 g (0.077 mol) of 3-chloro-2-phenylthio-5-trifluoromethyl-pyridine in 150 ml of glacial acetic acid, during which process the temperature climbed up to 30° C. in the course of 4 hours. The reaction mixture was stirred for 14 hours at 30–25° C., then poured into ice-water and worked up as described. This gave 24.6 g of a viscous oil which, according to HPLC check, contained 19.9 g (83.5% of theory) of the title compound and 1.4 g (5.6% of theory) of the corresponding sulfone. Chromatography with methylene chloride through a suction filter with flash silica gel yielded the pure title compound (18.2 g=76.6% of theory) of m.p. 79–80° C.
Variant b 11.76 g (0.173 mol) of 50% strength hydrogen superoxide were added at 25° C. in the course of 20 minutes to a mixture of 50 g (0.173 mol) of 3-chloro-2-phenylthio-5-trifluoromethylpyridine in 50 ml of trifluoroacetic acid and 250 ml of acetic acid. After the reaction mixture has been stirred at 30 to 28° C. for 4 hours, it was extracted with methylene chloride, and the organic phase was washed with sodium hydrogen carbonate solution and with water. Drying over magnesium sulfate and concentration in vacuo yielded 48.5 g of colorless crystals of m.p. 67–68° C. According to NMR analysis, they contained 44.9 g (85% of theory) of the pure title compound and 3.6 g (6.4% of theory) of the corresponding sulfone.

Example 6

3-Chloro-2-phenylsulfonyl-5-trifluoromethylpyridine
Variant a 25.1 g (0.369 mol) of 50% strength hydrogen superoxide were added at 35° C. in the course of 30 minutes with stirring to a mixture of 48.5 g (0.1675 mol) of 3-chloro-2-phenylthio-5-trifluoromethylpyridine in 300 ml of glacial acetic acid and stirred for 18 hours at 40° C. until the exothermal reaction had subsided to 25° C. After HPLC check of the course of the reaction, a further 5 g (0.0735 mol) of 50% strength hydrogen superoxide were added and the mixture was stirred for 2 hours at 40° C. The reaction mixture was poured into ice-water and worked up as described. This gave 49.2 g of the title compound as a crude oil which, after chromatography with methylene chloride through silica gel, solidified to give 44.5 g (82.6% of theory) of colorless crystals of m.p. 87–88° C.
Variant b 273.2 g (0.495 mol) of 13.5% strength sodium hypochlorite solution in 240 ml of water were added at 25–30° C. in the course of 2 hours to a mixture of 65.2 g (0.225 mol) of 3-chloro-2-phenylthio-5-trifluoromethylpyridine in 100 ml of water and 100 ml of glacial acetic acid. After the mixture had been stirred for 2 hours at 25° C., a further 70 ml of glacial acetic acid were added, and 84.5 g (0.153 mol) of 13.5% strength sodium hypochlorite solution were fed in over 30 minutes. After the reaction mixture had been stirred for 3 hours at 25° C., it was extracted with methylene chloride, and the organic extract was washed with water, saturated sodium hydrogen carbonate solution and again with water. The mixture was subsequently dried over magnesium sulfate and concentrated in vacuo. This gave 70.9 g (98% of theory) of the title compound of m.p. 91° C. According to GC check, the purity was 100%.

The protocols given in the above Synthesis Examples were used for obtaining further pyridine thioethers Ia and thiopyridines I by modifying the starting compounds as required. Selected physical data of the pyridine thioethers are listed in Table 10 and of the thiopyridines in Table 11.

TABLE 10

| No. | $R^1$ | $R^2$ | $n_D^{24}$ | Fp [° C.] |
|---|---|---|---|---|
| Ia2.003 | $CF_3$ | n-$C_3H_7$ | 1.5120 | |
| Ia2.008 | $CF_3$ | tert-$C_4H_9$ | 1.5069 | |
| Ia2.015 | $CF_3$ | n-$C_6H_{13}$ | 1.5031 | |
| Ia2.029 | $CF_3$ | n-$C_{10}H_{21}$ | 1.4930 | |
| Ia2.062 | $CF_3$ | phenyl | 1.5750 | |
| Ia2.065 | $CF_3$ | 4-chlorophenyl | | 63–65 |
| Ia2.073 | $CF_3$ | 4-tolyl | 1.5725 | |
| Ia2.080 | $CF_3$ | 4-methoxyphenyl | | 81–83 |
| Ia2.105 | $CF_3$ | benzyl | 1.5645 | |
| Ic4.062 | $CF_2H$ | phenyl | | 50–53 |
| Ic5.062 | $NO_2$ | phenyl | | 103–104 |

TABLE 11

| No. | $R^1$ | $R^2$ | $n_D^{24}$ | Fp [° C.] |
|---|---|---|---|---|
| Ib2.003 | $CF_3$ | n-$C_3H_7$ | | 51–53 |
| Ib2.015 | $CF_3$ | n-$C_6H_{13}$ | 1.5053 | |
| Ib2.062 | $CF_3$ | phenyl | | 79 14 80 |
| Ib2.065 | $CF_3$ | 4-chlorophenyl | | 124–125 |

TABLE 11-continued

| No. | $R^1$ | $R^2$ | $n_D^{24}$ | Fp [° C.] |
|---|---|---|---|---|
| Ib2.073 | $CF_3$ | 4-tolyl | | 73–75 |
| Ib2.105 | $CF_3$ | benzyl | | 102–103 |
| Ic2.003 | $CF_3$ | n-$C_3H_7$ | | 41–42 |
| Ic2.015 | $CF_3$ | n-$C_6H_{13}$ | 1.4877 | |
| Ic2.062 | $CF_3$ | phenyl | | 89–91 |
| Ic2.065 | $CF_3$ | 4-chlorophenyl | | 105–108 |
| Ic2.073 | $CF_3$ | 4-tolyl | | 65–68 |
| Ic4.062 | $CF_2H$ | phenyl | | 69–72 |
| Ic5.062 | $NO_2$ | phenyl | | 158–159 |

Use Example

3-Chloro-2-phenylsulfonyl-5-trifluoromethylpyridine was stirred with 4-chloro-2-fluoro-5-methoxyphenylmagnesium bromide for 2.5 hours at room temperature in THF. Working-up by distillation gave the coupling product 2-(4-chloro-2-fluoro- 5-methoxyphenyl)-3-chloro-5-trifluoromethylpyridine in a yield of 84%, which is outstanding.

Further herbicidally active ingredients disclosed in WO 95/02580 are obtained in a simple manner by eliminating the methoxy group in the 5-position on the benzene ring and other, prior-art subsequent reactions.

We claim:

1. A substituted thiopyridine of the general formula I

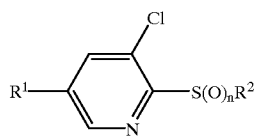

where
n is 1 or 2;
$R^1$ is chlorine, trifluoromethyl or difluoroethyl;
$R^2$ is a $C_1$–$C_8$-alkyl radical which is unsubstituted or substituted by chlorine or methoxy, or a benzyl or phenyl radical which is unsubstituted or substituted in the phenyl moiety by chlorine, methyl or trifluoromethyl, with the exception of the compound: 3,5-dichloro-2-methylsulfinylpyridine.

2. A process for the preparation of thiopyridines of the general formula Ic

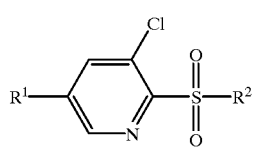

as defined in claim 1, which comprises reacting a 3-chloro-2-halopyridine of the formula II,

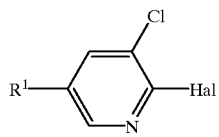

where $R^1$, has the meaning mentioned in claim 1 and Hal is fluorine, chlorine, or bromine, with an alkali metal or alkaline earth metal salt of a thio compound of formula III

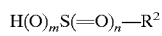

where $R^2$ in formula III has the meaning mentioned in claim 1 and m and n are 0 or 1, and, in the event that m and n have the value 0, subsequently treating the product of this reaction, pyridine thioether Ia,

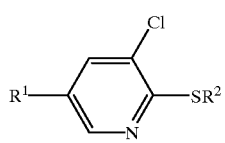

with an oxidant.

3. A process as defined in claim 2, wherein the oxidation of the pyridine thioethers Ia to give the thiopyridines I is effected with the aid of hydrogen peroxide in a mixture of acetic acid and trifluoroacetic acid in a ratio of 6:1 to 4:1 by volume.

4. A process as defined in claim 2, wherein the oxidation of the pyridine thioethers Ia to give the thiopyridines I is effected with the aid of hypochlorous acid and an alkali metal salt thereof.

5. A pyridine thioether of the general formula Ia

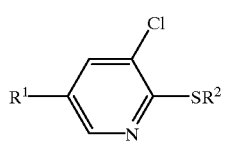

where
$R^1$ is chlorine, trifluoromethyl or difluoromethyl;
$R^2$ is a $C_1$–$C_8$-alkyl radical which is unsubstituted or substituted by chlorine or methoxy, or a benzyl or phenyl radical which is unsubstituted or substituted in the phenyl moiety by chlorine, methyl, methoxy or trifluoromethyl,
with the exception of the compounds:
2-(2-methyl-4-methoxyphenylthio)-3-chloro-5-trifluoromethylpyridine and 2-(3-methyl-4-methoxyphenylthio)-3-chloro-5-trifluoromethylpyridine.

* * * * *